United States Patent [19]

Bauer

[11] 4,259,441

[45] Mar. 31, 1981

[54] PROCESS FOR RESOLVING D, L-LEUCINE

[75] Inventor: Dennis P. Bauer, Baton Rouge, La.

[73] Assignee: Ethyl Corporation, Richmond, Va.

[21] Appl. No.: 76,211

[22] Filed: Sep. 17, 1979

[51] Int. Cl.³ .......................... C12Q 1/38; C07B 19/02
[52] U.S. Cl. ..................................... 435/23; 435/116; 435/280
[58] Field of Search .......................... 435/23, 116, 280

[56] References Cited

U.S. PATENT DOCUMENTS

| 3,031,380 | 4/1962 | Minagawa et al. | 435/280 |
|---|---|---|---|
| 3,813,317 | 5/1974 | Benoiton et al. | 435/280 |
| 3,907,638 | 9/1975 | Uzuki et al. | 435/280 |
| 3,963,573 | 6/1976 | Stauffer | 435/280 |

FOREIGN PATENT DOCUMENTS 660817 11/1951 United Kingdom ..................... 435/280

OTHER PUBLICATIONS

Journal of Biol. Chem., vol. 243, No. 7, pp. 1344–1348 (1968).
Kirk–Othmer, Encyclopedia of Chemical Technology, 2nd Ed., vol. 2, J. Wiley & Sons, Inc., New York, pp. 156–197.
"Synthetic Production & Utilization of Amino Acids", by J. Wiley & Sons, N.Y., pp. 136–140 (1974).
Greenstein et al., "Chemistry of the Amino Acids", vol. 3, J. Wiley & Sons, N.Y., pp. 2080–2085 (1961).
Guntelberg et al., "Purification of the Proteolytic Enzyme from Bacillus Subtilis", C. R. Trav. Lab., Carlsberg, Ser. Chim. 29 (1954).
Subramanian et al., "The Major Alkaline Proteinase of Aspergillus Oryzae, Aspergillopeptidene", Biochem. vol. 3, No. 12., pp. 1861–1874 (1964).
Journal of Biol. Chem., vol. 241; pp. 5974–5976 (1966).
Journal of Biochemistry vol. 62, No. 6, pp. 633–641 (1967).
Agr. Biol. Chem., vol. 31, No. 10, pp. 1151–1158 (1967).
Agr. Biol. Chem., vol. 34, No. 9, pp. 1383–1392 (1970).

*Primary Examiner*—Benoit Castel
*Attorney, Agent, or Firm*—Donald L. Johnson; John F. Sieberth; James M. Pelton

[57] ABSTRACT

Production of optically pure D-leucine and L-leucine ester by treating a racemic mixture of N-acyl-D,L-leucine ester with a proteolytic enzyme and separating the resulting N-acyl-L-leucine and N-acyl-D-leucine ester from the solution with subsequent removal of the N-acyl and ester groups to provide L-leucine and D-leucine, respectively.

9 Claims, No Drawings

PROCESS FOR RESOLVING D, L-LEUCINE

BACKGROUND OF THE INVENTION

This invention relates to a process for resolving mixtures of D,L-leucine. Specifically, N-acyl-D,L-leucine ester mixtures can be selectively enzymatically hydrolyzed and, as a result, separated into the D- and L-optical antipodes.

Synthetic, racemic D,L-amino acids can be utilized under conditions which vary with the case in question. Man can utilize the D-forms of amino acids as a racemic mixture and by conversion of D-form to L-form. However, various animals have varying utilization efficiencies for the D- or L-forms of amino acids. Specifically, the rat and the mouse utilize L-leucine alone, whereas, in the chick, D,L-leucine and L-leucine are equally well utilized for growth.

It should also be noted that for growth, maintenance, reproduction and tissue repair, organisms require a supply of qualitatively and quantitatively specific amino acids. One of the essential amino acids is leucine. As a racemic mixture, it can be used by the body, but in its L-form it is more useful to combat malnutrition and for supplementation of a deficient diet. Thus, there is a need for processes which conveniently resolve racemic mixtures of D,L-leucine.

Several principles have been applied in the resolution of D,L-forms of amino acids into their D and L components. Conventional procedures for such separations include (1) direct crystallization, for example, by seeding a highly concentrated solution of D,L-threonine with a known amount of L-threonine, the L-form will crystallize out; (2) crystallization with an optically active reagent in polarized light, for example, the alkaloids, bases and optically active reagents in polarized light can form derivatives having different solubilities; and (3) enzymatic methods. In this last method, some enzymes behave differently with respect to the D and L-forms of amino acids. Thus, orginase acts only on the L-isomer, the D-isomer remaining intact in the solution from which it may then be extracted. Also, the L-amino acid oxidases may be used to extract D-leucine, D-methionine and D-phenylalanine. *Kirk-Othmer, Encyclopedia of Chemical Technology,* Second Edition, Vol. 2, John Wiley & Sons, Inc., New York, pp. 156-197.

Specifically, a number of methods for the optical resolution of D,L-leucine are known. For example, the physicochemical resolution by preferential crystallization of either one of the optically active isomers from a supersaturated solution of acetyl-D,L-leucine is known. In the case of enzymatic resolution, acetyl-D,L-leucine can be asymmetrically hydrolyzed by treatment with aminoacylase obtained from hog kidney or moulds. Optical resolution is then possible in good yield by separating the resultant products, L-leucine and acetyl-D-leucine. Such asymmetric hydrolysis has also been achieved with insolubilized mould aminoacylase. Kaneko et al, *Synthetic Production and Utilization of Amino Acids,* J. Wiley & Sons, New York (1974), p. 136-140.

In U.S. Pat. No. 3,963,573, there is taught a process for producing optically pure N-acyl-L-methionine by subjecting an N-acyl-D,L-methionine ester to the action of a proteolytic enzyme selected from the group consisting of sulfhydryl proteinases and microbially derived serine proteinases and separating the resulting N-acyl-L-methionine. The art has recognized that certain proteolytic enzymes can be produced in a pure form, such as from *Bacillus subtilis, Guntelberg Trav. Lab. Carlsberg,* Ser. Chim. Vol. 29, p. 36-48 (1954). The proteolytic enzyme prepared from the strain of *Bacillus subtilis* was purified by crystallization and its physicochemical properties were determined. The enzymatic properties were investigated insofar as optimum pH for milk coagulation, stability, degradation of casein, hydrolysis of hemoglobin, activators and inhibitors for the enzymes, the effect on ovalbumin and other characteristics. In the *Journal of Biological Chemistry,* Vol. 243, No. 7, pp. 1344-1348 (1968) Barel, examined the activity of Carlsberg and Novo subtilisins toward a number of N-acetylamino acid esters and amino acid esters. The enzymes were also compared with respect to their efficiency in catalyzing aminolysis reactions, their rates of inactivation by certain aromatic sulfonyl halides and the rates of deacylation of their N-trans-cinnamoyl derivatives. Although the enzymes were found qualitatively indistinguishable from the standpoint of substrate specificity, significant quantitative differences were observed. Thus, the microbially derived serine proteinases, for example, Novo and Carlsberg subtilisin exhibited varying of degrees of esterase activity on various N-acyl-L-amino acid esters. However, there is not disclosed a process for resolution of N-acyl-D,L-leucine esters employing the activity of serine proteinases. An especially effective process would involve (1) readily available and inexpensive material, such as enzyme, and (2) produce high purity material in high yield at a rapid rate.

SUMMARY OF THE INVENTION

This invention provides an especially effective process for resolving D,L-leucine when in the form of the N-acyl ester derivatives, obtaining N-$C_{1-9}$ acyl-D-leucine ester and N-$C_{1-9}$ acyl-L-leucine which can be subsequently converted to D-leucine and L-leucine, respectively. In one aspect of this invention, there is provided a process for resolving a racemic mixture of D,L-leucine, said process comprising the steps of (a) acylating a racemic mixture of D,L-leucine to form a mixture of N-acyl-D,L-leucine, (b) esterifying the resultant N-acyl-D,L-leucine to form a mixture of N-acyl-D,L-leucine esters, (c) subjecting the resultant mixture of N-acyl-D,L-leucine esters to the action of a proteolytic enzyme selected from the group consisting of microbially derived serine proteinases, (d) separating the unreacted N-acyl-D-leucine ester from the resulting N-acyl-L-leucine, and (e) from the separate N-acyl-D-leucine ester and N-acyl-L-leucine, recovering D-leucine and L-leucine, respectively.

DETAILED DESCRIPTION OF PREFERRED EMBODIMENTS

As indicated above, this invention relates to a process for producing optically pure D-leucine and L-leucine comprising (a) establishing a solution of N-acyl-D,L-leucine esters, (b) subjecting the solution to the action of a proteolytic enzyme selected from the group consisting of microbially derived serine proteinases, (c) separating the unreacted N-acyl-D-leucine ester from the resulting N-acyl-L-leucine, and (d) treating the separated N-acyl-D-leucine ester and N-acyl-L-leucine to recover D-leucine and L-leucine, respectively.

As used herein, "optically pure D-leucine and L-leucine" means D-leucine substantially free of the L-isomer and L-leucine substantially free of the D-isomer.

It has been found that certain readily available proteinases, namely, microbially derived serine proteinases exhibit high esterase activity for N-acyl-L-leucine esters. Furthermore, it has been found that the high esterase activity exhibited for the L-isomer is not inhibited by the presence of the D-isomer. Subjecting N-acyl-D,L-leucine ester to the action of such a proteinase provides a mixture of N-acyl-D-leucine ester and N-acyl-L-leucine. The N-acyl-L-leucine can be readily separated from the mixture by conventional means, for example, by adjusting the pH of an aqueous mixture thereof and extracting with an organic solvent such as chloroform, ethyl acetate, butyl acetate, methylene chloride and the like.

A variety of specific N-acyl-D,L-leucine ester mixture can be employed in this invention. Preferably, compounds will have the acyl and ester groups mentioned hereinbelow.

Preferably, the acyl group is derived from carboxylic acids containing from 1 to 9 carbon atoms. More particularly, the N-acyl group will preferably be formyl, acetyl, propionoyl, butyroyl, valeroyl, caproyl, enanthoyl, capryryl, or pelargonoyl. The ester group can be derived from a variety of alcohols containing from 1 to 10, preferably from 1 to 6, carbon atoms. Especially suitable examples of ester groups are methyl, ethyl, n-propyl, isopropyl, n-butyl, sec. butyl, isobutyl, pentyl and hexyl. Especially suitable examples of acyl groups are formyl, acetyl and propionyl. Racemic N-acetyl-D,L-leucine methyl ester is most preferred for use in the process of this invention.

Serine proteinases suitable for use in this invention are derived from microorganisms such as bacteria, fungi and mold. Microbially derived serine proteinases are preferred for use in the process of this invention. These proteinases are relatively inexpensive and commercially available.

An example of preferred serine proteinases for use in this invention are those derived from the bacterial organism *Bacillus subtilis* and termed subtilisins.

A preferred subtilisin of the present invention is the *Bacillus subtilis*-derived Carlsberg strain. The Carlsberg strain employed in accordance with the present invention is a known subtilisin strain, the amino acid sequence of which is described in Smith et al, "The Complete Amino Acid Sequence of Two Types of Subtilisin, BPN' and Carlsberg," *J. of Biol. Chem.*, Vol. 241, Dec. 25, 1966, at Page 5974. This subtilisin strain is characterized by a tyrosine to tryptophan ratio of about 13:1. The above reference including its description of the amino acid sequence of the Carlsberg subtilisin is hereby incorporated by reference.

An X-ray mutated *Bacillus subtilis*-derived subtilisin constitutes another preferred subtilisin of the present invention. This mutation can be effected in accordance with U.S. Pat. No. 3,031,380, issued Apr. 24, 1962, to Minagawa et al by irradiation of a *Bacillus subtilis* organism with X-rays. Subsequent treatment in a conventional manner can be employed to result in the preparation of an enzymatic composition. The patent describes a process whereby an enzymatic composition is produced by subjecting *Bacillus subtilis* to X-rays of an intensity corresponding substantially to 24–50 roentgens for an interval of at least half an hour, selecting from the colony thus subject to X-rays a strain identified by cells having hairless, rough, jagged, spotted and dull white characteristics, separating said strain and placing the separated strain in a culture selected from the group consisting of wheat bran and corn meal, maintaining the culture for a period of at least 40 hours while aerating the culture substantially continuously, and drying the culture. The disclosure of U.S. Pat. No. 3,031,380 is hereby incorporated by reference.

Other examples of suitable serine proteinases for use herein include the following. Serine proteinases derived from *Aspergillus oryzae*. Methods for producing and separating these mold derived enzymes are known to those skilled in the art. See, for example, Subramamian et al, *Biochemistry*, Vol. 3, No. 12, Pages 1861–74 (1964), and Misaki et al, *Agr. Biol. Chem.*, Vol. 34, No. 9, Pages 1383–92 (1970). Serine proteinase derived from *Streptomyces griseus* (ATCC 3463). Such serine proteinases are available commercially under the tradename "Pronase" from Kaken Chemical Co., Japan. Methods for producing and separating the proteinases are known. See, for example, Narashashi et al, *The Journal of Biochemistry*, Vol. 62, [N]. 6, Pages 633–41 (1967). Serine proteinase derived from *Aspergillus sydowi*. Methods for producing and separating this fungally derived serine proteinase are known. See, for example, Danno et al, *Agr. Biol. Chem.*, Vol. 31, No. 10, Pages 1151–58 (1967).

Other suitable examples of microbially derived serine proteinases are Aspergillus alkaline proteinase (E. C. 3.4.21.15), Alternaria endopeptidase (E. C. 3.4.21.16), Arthrobacter serine proteinase (E. C. 3.4.21.17). These particular enzymes have been identified according to a systematic nomenclature involving an "E. C. number". See "Enzyme Nomenclature", Commission of Biochemical Nomenclature, Elsevier Publishing Company (1973), U.S. Library of Congress Card No. 73-78247.

The action of the proteolytic enzyme on the N-acyl-D,L-leucine ester is very suitably conducted in an aqueous medium maintained at a pH of from about 5 to about 10, preferably from about 7 to about 8, and at a temperature of from about 10° to about 60° C. Preferably, the temperature is maintained in the range of from about 20° to about 40° C.

Because of the highly selective esterase activity of the particular proteolytic enzymes employed in this invention toward N-acyl-L-leucine ester in N-acyl-D,L-leucine ester mixtures, very small amounts of the proteolytic enzyme are necessary in order to rapidly produce N-acyl-L-leucine and separate it from N-acyl-D-leucine ester. For example, aqueous solutions containing from about 0.0005% to about 1.0%, by weight, preferably from about 0.005% to about 0.5%, by weight, of enzymes are employed. The amounts of enzyme referred to herein refer to pure crystalline enzyme.

The amount of N-acyl-D,L-leucine ester employed will generally be at least about 5%, by weight, of the aqueous solution. Preferably, larger amounts are employed, for example, amounts up to and exceeding the maximum solubility of the N-acyl-D,L-leucine ester in the aqueous medium. Preferably, about 10 weight percent of N-acyl-D,L-leucine ester in the aqueous solution is preferred. Amounts slightly exceeding the maximum solubility can be employed since as the L-isomer is consumed by the action of the enzyme more will enter solution.

The rate of the action of the enzyme on the material will depend on the concentration of the enzyme and ester in solution. In this regard, N-acetyl-D,L-leucine methyl ester is quite suitable in that it exhibits good solubility in water (about 20% by weight at pH 7.5 and 25° C.). Therefore, N-acetyl-D,L-leucine methyl ester is a preferred ester substrate of this invention and a detailed specific embodiment of the invention employing this material is provided in the following example.

In general, the process of the present invention includes first preparing the N-acyl derivative of D,L-leucine by reacting, for example, with an organic acid anhydride in an alkaline or basic system. The N-acyl-D,L-leucine is then acidified in the presence of a suitable alcohol to prepare the N-acyl-D,L-leucine ester. This ester is then selectively hydrolyzed with the desired microbially derived serine proteinase to form a mixture of N-acyl-D-leucine ester and N-acyl-L-leucine. The resultant mixture is then separated, for example, by extraction of the N-acyl-D-leucine ester into an organic solvent and the separated N-acyl-D-leucine ester is deesterified and the acyl group removed to recover D-leucine, if desired. The N-acyl-L-leucine remaining in the aqueous solution can have the water evaporated and be used as such for dietary supplementation. Alternatively, the acyl group can be removed by conventional procedures to produce L-leucine per se.

The following example of the process of the present invention is non-limiting and illustrative only. Purely for convenience in illustration, the example employs the acetyl group as the acyl group and the methyl group as the esterifying group.

EXAMPLE

Part A: Preparation of N-acetyl-D,L-leucine

Into a 250 milliliter round bottom flask were placed 13.1 grams (100 millimoles) of D,L-leucine, 4.40 grams (110 millimoles) of NaOH and 35 milliliters of methanol to make a stirrable slurry. To this mixture was slowly added with stirring, 13.2 g (130 millimoles) of acetic anhydride. This mixture was continuously stirred until the slurry turned to a clear solution. The resulting clear solution contained N-acetyl-D,L-leucine.

Part B: Preparation of N-acetyl-D,L-leucine Methyl Ester

Into a 100 milliliter round bottom flask were placed 17.3 grams (0.1 moles) of N-acetyl-D,L-leucine, 64 grams (2.0 moles) of absolute methanol and 2 grams (0.02 moles) of sulfuric acid. The mixture was stirred and refluxed for 4 hours then cooled to room temperature. The solvent was then removed under vacuum and the resulting oily residue was taken up in 100 milliliters of ether, washed with 5% sodium bicarbonate, and then 50 milliliters of saturated sodium chloride solution. The ether layer was dried over magnesium sulfate, filtered and the solvent removed in vacuo to leave an oily residue. The oily residue was triturated with 50 milliliters of petroleum ether for 10 minutes whereupon the oil crystallized. The white mass was filtered and vacuum dried. Yield of the white product, N-acetyl-D,L-leucine methyl ester, was 85%. The proton NMR and infrared spectra agreed with the conclusion that the methyl ester of N-acetyl-D,L-leucine was prepared.

Part C: Separation of N-acetyl-D-leucine Methyl Ester and N-acetyl-L-leucine

Into a 100 milliliter beaker were placed 1.87 grams (10 millimoles) of N-acetyl-D,L-leucine methyl ester and 15.83 grams (10 wt %) of water. The slurry was adjusted to pH 7.5 with 0.2 N sodium hydroxide. Then, 00.1 grams (0.05 wt % based on the aqueous solution) of purified Carlsberg subtilsin, a serine proteinase commercially available under the tradename "Alcalase" from Novo Industries, Copenhagen, Denmark, was added with stirring. The pH of the solution immediately decreased and was readjusted to pH 7.5 and maintained at this level until enzyme activity ceased after about 11 minutes. A total of 25.1 milliliters of 0.2 N sodium hydroxide was delivered.

The reaction mixture was extracted twice with 100 milliliters of methylene chloride. The organic extracts were combined, dried and the solvent removed under vacuum to yield 0.90 grams of N-acetyl-D-leucine methyl ester. The yield was 96.2%, proton NMR and infrared spectra confirmed the structure. The optical purity obtained was 95.7%.

The aqueous layer from the extracts was acidified to a pH of 1 by dropwise addition of concentrated sulfuric acid. It was then extracted four times with 100 milliliter portions of ethyl acetate. The organic extracts were combined, dried and solvent removed in vacuo to yield 0.85 gram of N-acetyl-L-leucine for 91% yield. Proton NMR confirmed the structure and the optical purity of N-acetyl-L-leucine was 96.7%.

Thus, the racemic solution can be separated and substantially pure N-acetyl-D-leucine methyl ester can be obtained. This example represents the comprehensive procedure for obtaining optically pure N-acetyl-D-leucine methyl ester. It should be understood by a skilled artisan that a variety of methods are available for forming N-acyl-D,L-leucine esters and a variety of methods are also available for separating mixtures of N-acyl-D-leucine esters and N-acyl-L-leucine.

The foregoing example can be repeated employing serine proteinases such as subtilisin BPN, BPN' or *Aspergillus oryzae* derived proteinase with similar results. Further, the ester group can be methyl, ethyl, propyl, or isopropyl esters of N-formyl-D, L-leucine; ethyl, propyl or isopropyl esters of N-acetyl-D,L-leucine; methyl, ethyl, propyl or isopropyl esters of N-propionyl-D,L-leucine. Similar results are obtained in production of optically pure N-(formyl, acetyl or propionyl)-D-leucine esters which can be separated from the N-(formyl, acetyl or propionyl)-L-leucine.

The N-acyl-D-leucine ester or N-acyl-L-leucine provided by the process of this invention can be converted by a simple procedure to D-leucine and L-leucine, respectively. In one procedure, treatment at elevated temperatures with dilute acid can be employed, for example, by dissolving in 2 N HBr and the resultant solution being warmed for a time at 80°–100° C. Other simple hydrolysis procedures can be employed to convert the N-acyl-D-leucine esters and N-acyl-L-leucine into the desired D-leucine and L-leucine, respectively.

Having described the process of this invention, it is clear that skilled artisans will recognize many variations within the scope and spirit of the invention. Therefore, it is desired that the invention be limited only by the lawful scope of the following claims.

What is claimed is:

1. A process for resolving a racemic mixture of D,L-leucine, said process comprising the steps of
   (a) acylating a racemic mixture of D,L-leucine to form a mixture of N-acyl-D,L-leucine,
   (b) esterifying the resultant N-acyl-D,L-leucine to form a mixture of N-acyl-D,L-leucine ester, (c) subjecting the resultant mixture of N-acyl-D,L-leucine esters to the action of a proteolytic enzyme selected from the group consisting of microbially derived serine proteinases, (d) separating the unreacted N-acyl-D-leucine ester from the resulting N-acyl-L-leucine, and (e) recovering D-leucine and L-leucine from the separate N-acyl-D-leucine ester and N-acyl-L-leucine, respectively.

2. The process of claim 1 wherein the acyl group contains from 1–9 carbon atoms.

3. The process of claim 2 wherein the ester group contains from 1–10 carbon atoms.

4. The process of claim 1 wherein the proteolytic enzyme is a microbially derived serine proteinase which is subtilisin Carlsberg.

5. The process of claim 1 wherein the mixture of N-acyl-D,L-leucine ester comprises N-acetyl-D,L-leucine methyl ester.

6. The process according to claim 1 in which said step (c) is further characterized by subjecting an aqueous solution of a racemic mixture of N-acetyl-D,L-leucine methyl ester to the action of a proteolytic enzyme selected from the group consisting of microbially derived serine proteinases at a pH in the range of from 5 to 10.

7. The process according to claim 6 which is carried out at a pH in the range from about 5 to about 7.5 and at a temperature in the range from about 10° C. to about 60° C.

8. The process according to claim 7 further characterized by the serine proteinase being subtilisin Carlsberg.

9. The process according to claim 8 wherein the proteinase is subtilisin Carlsberg and the temperature is in the range from about 20° C. to about 40° C.

* * * * *